United States Patent
Oxman et al.

(10) Patent No.: US 7,537,452 B2
(45) Date of Patent: May 26, 2009

(54) PHOTOINITIATOR SYSTEMS WITH ANTHRACENE-BASED ELECTRON DONORS FOR CURING CATIONICALLY POLYMERIZABLE RESINS

(75) Inventors: Joel D. Oxman, Minneapolis, MN (US); Karsten Dede, Landsberg (DE); Craig A. Dykstra, St. Paul, MN (US); Victoria A. Russell, Brooklyn Park, MN (US); Christoph Thalacker, Weilheim (DE); Wolfgang Weinmann, Weilheim (DE)

(73) Assignees: Curators of the University of Missouri, Columbia, MO (US); 3M Innovative Properties Company 3M Center, St. Paul, MN (US); 3M ESPE AG, Seefeld (DE)

( * ) Notice: Subject to any disclaimer, the term of this patent is extended or adjusted under 35 U.S.C. 154(b) by 0 days.

(21) Appl. No.: 11/893,457

(22) Filed: Aug. 16, 2007

(65) Prior Publication Data

US 2007/0287764 A1 Dec. 13, 2007

Related U.S. Application Data

(62) Division of application No. 10/719,598, filed on Nov. 21, 2003, now Pat. No. 7,262,228.

(51) Int. Cl.
*A61C 5/00* (2006.01)
*C08K 3/18* (2006.01)
*C08G 59/00* (2006.01)
*C08G 64/00* (2006.01)
*C08G 65/00* (2006.01)
*C08F 2/50* (2006.01)

(52) U.S. Cl. .......... 433/228.1; 522/15; 522/23; 522/25; 522/83; 522/168; 522/170; 522/181; 522/178

(58) Field of Classification Search ............ 522/15, 522/25, 23, 83, 168, 170, 178, 181; 433/228.1
See application file for complete search history.

(56) References Cited

U.S. PATENT DOCUMENTS 3,729,313 A * 4/1973 Smith ............... 430/332
4,256,828 A 3/1981 Smith
4,394,403 A 7/1983 Smith
4,560,709 A 12/1985 Berner et al.
4,835,193 A 5/1989 Hayase et al.
5,206,116 A * 4/1993 Daniels et al. ............ 430/311
5,545,676 A 8/1996 Palazzott et al.
5,639,802 A 6/1997 Neckers et al.
5,856,373 A 1/1999 Kaisaki et al.
5,980,253 A 11/1999 Oxman et al.
6,025,406 A 2/2000 Oxman et al.
6,043,295 A 3/2000 Oxman et al.
6,084,004 A 7/2000 Weinmann et al.
6,395,124 B1 * 5/2002 Oxman et al. ........... 156/275.5
6,706,403 B1 * 3/2004 Olofson et al. ............ 428/413
6,747,071 B1 6/2004 Frances
6,765,036 B2 * 7/2004 Dede et al. ................. 522/15
6,949,297 B2 * 9/2005 Yang et al. ................. 428/520
7,262,228 B2 * 8/2007 Oxman et al. .............. 522/25
2003/0035899 A1 2/2003 Klettke et al.
2003/0166737 A1 9/2003 Dede et al.

FOREIGN PATENT DOCUMENTS

EP 1133971 9/2001
WO WO 00/19966 4/2000
WO WO 03/059295 7/2003

OTHER PUBLICATIONS

Crivello J. V., Jang M., *Anthracene electron-transfer photosensitizers for onium salt induced cationic photopolymerizations*, Journal of Photochemistry and Photobiology A: Chemistry, vol. 159 No. 2, 14 173-188 (Jul. 2003).

* cited by examiner

*Primary Examiner*—Susan W Berman
(74) *Attorney, Agent, or Firm*—Stinson Morrison Hecker LLP

(57) ABSTRACT

The invention features a photopolymerizable composition that comprises a cationically polymerizable resin, and a photoinitiator system comprising an iodonium salt, a visible light sensitizer, and one or more anthracene-based compounds as electron donors. Electron donor combinations used in the invention include multiple substituted anthracene compounds or a combination of at least one substituted anthracene compound with unsubstituted anthracene.

54 Claims, No Drawings

PHOTOINITIATOR SYSTEMS WITH ANTHRACENE-BASED ELECTRON DONORS FOR CURING CATIONICALLY POLYMERIZABLE RESINS

CROSS-REFERENCE TO RELATED APPLICATIONS

This application is a divisional application of U.S. patent application Ser. No. 10/719,598, which was filed on Nov. 21, 2003 now U.S. Pat. No. 7,626,228, which is incorporated by reference in its entirety.

FIELD OF THE INVENTION

In general, this invention relates to a photoinitiator system for cationically polymerizable resins. More specifically, this invention relates to photopolymerizable compositions that contain a cationically polymerizable resin and an anthracene-based photoinitiator system that is activated upon exposure to actinic radiation. This invention also relates to methods of polymerizing such compositions using this photoinitiator system.

BACKGROUND OF THE INVENTION

Since the 1950's, the dental industry has invested a great deal of effort into the research and development of tooth-colored alternatives to metal amalgam for the restoration of teeth. The use of acrylic (e.g., poly(methyl methacrylate) or PMMA) was a first step toward the use of polymer technology for tooth restoration. Many of the current dental restorative systems are based on dimethacrylate monomer resins containing silane-treated inorganic filler particles (such as barium, strontium, zirconium glasses or quartz) and are cured via free-radical polymerization.

Methacrylate composites were first introduced as two-component systems that were chemically cured. One component of the system typically contains a peroxide, the other an amine. When mixed together the two initiator components react to create free radicals and initiate polymerization of the methacrylate matrix. This procedure requires substantial mixing time before application and offers limited contouring time before the composite is cured. The introduction of initiator systems that produced free radicals via visible light (400-1000 nm) absorption attempted to address these problems by permitting the use of single-component restorative systems that were cured after contouring.

Unfortunately these light-cured methacrylate restoratives can exhibit significant shrinkage during photopolymerization, which can lead to the build-up of stress within the composite and at the composite-tooth interface. These stresses can become high enough to result in cusp fracture, marginal failure, and/or post-operative sensitivity. For this reason, incremental placement and curing of light curing composites is a common dental practice. This process allows for minimization of stress/shrinkage related complications, but also increases the amount of working time required for a successful restoration.

Previous research has focused on the development of low-shrink restoratives as an alternative to incremental placement techniques. The use of aliphatic epoxy monomers as dental resins is one promising solution. These materials generally have, on the average, at least 1 polymerizable epoxy group per molecule, usually at least 2, and sometimes as many as 4 or more polymerizable epoxy groups per monomer. These epoxies utilize a cationic ring-opening polymerization curing mechanism.

Epoxy-containing compounds are known to be curable using various cationic initiator systems. For example, ternary photoinitiator systems comprising an iodonium salt, a visible light sensitizer, and an electron donor have been developed for curing of epoxy resins and epoxy/polyol resins. Although these systems have shown much promise, it is desirable to increase cure speed and depth of cure, and to provide for better color formation and sensitivity to temperature. Thus, a need remains for photopolymerizable compositions capable of providing satisfactory cure speed and depth of cure, while at the same time minimizing unwanted color formation and exhibiting good color stability.

SUMMARY OF THE INVENTION

The present invention features a photoinitiator system for a cationically polymerizable resin. In one embodiment, the system includes the following components: (a) an iodonium salt; (b) a visible light sensitizer; (c) a first anthracene that has a light absorption maximum less than about 400 nanometers; and (d) a second anthracene having the following structure:

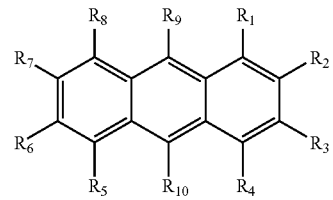

wherein each of $R_1$ to $R_{10}$ is independently selected from H, alkyl, phenyl or alkoxy groups, provided that at least one of $R_1$ to $R_{10}$ is not H. The first anthracene may be, for example, unsubstituted anthracene and the second anthracene may be an alkyl or alkoxy substituted anthracene, such as 2-ethyl-9,10-dimethoxyanthracene (EDMOA), 2,6-di-tert-butylanthracene or 9,10-dimethylanthracene. Additional anthracenes may optionally be present.

In another embodiment, the photoinitator system comprises a combination of two or more substituted anthracenes, wherein one of the anthracenes is an alkoxy substituted anthracene (e.g., EDMOA) and the other anthracene is an alkyl, phenyl or alkoxy substituted anthracene.

In yet another embodiment, the photoinitiator system comprises an alkoxy substituted anthracene such as 2-ethyl-9,10-dimethoxyanthracene, 9,10-diethoxyanthracene, 1,4-dimethoxyanthracene or 9,10-dimethoxyanthracene as the electron donor with or without any additional anthracene-based compounds or other electron donors being present in the composition.

The photoinitiator systems of the invention may be combined with a cationically polymerizable resin in order to provide a photopolymerizable composition. The cationically polymerizable resin may be selected from epoxy, oxetane, vinyl ether and spiro-orthocarbonate resins, and combinations thereof. In some embodiments, the cationically polymerizable resin comprises an epoxy resin, such as a silicon-containing epoxy resin, or a blend of a silicon-containing epoxy resin and an epoxy resin that does not contain silicon. Optionally, the photopolymerizable composition may further comprise a free-radically polymerizable resin and/or a hydroxyl-containing material.

The iodonium salt for the photoiniator system may be, for example, diaryliodonium hexafluorophosphate, diaryliodonium hexafluoroantimonate, diaryliodonium tetrakis(pentafluorophenyl)borate, 4-octyloxyphenyl phenyliodonium hexafluoroantimonate, 4-(2-hydroxytetradecyloxyphenyl) phenyliodonium hexafluoroantimonate, 4-(1-methylethyl) phenyl 4-methylphenyliodonium tetrakis(pentafluorophenyl)borate, or combinations thereof.

The visible light sensitizer may be selected from ketones, coumarin dyes, xanthene dyes, fluorone dyes, fluorescein dyes, aminoketone dyes, p-substituted aminostyryl ketone compounds, and combinations thereof.

By using selected anthracene-based compounds, or combinations thereof, as electron donors, the present invention achieves superior cure speed and color formation as compared to previously reported epoxy resin systems. A preferred donor composition comprises a mixture of a substituted anthracene such as 2-ethyl-9,10-dimethoxyanthracene, 2,6-di-tert-butylanthracene or 9,10-dimethylanthracene and unsubstituted anthracene. In general, the mixed donor systems show enhanced performance characteristics compared to systems that contain either of the individual electron donors by itself. This indicates a complimentary or synergistic reaction mechanism for electron donation when multiple anthracene donors are present in the photoinitiator system. This allows one to carefully tailor donor mixtures and concentrations to obtain optimum cure speed and cure depth while at the same time maintaining minimal amounts of objectionable color formation to a degree that has not been possible with previous initiator systems. Furthermore, the initiator systems of this invention have been found to provide photocurable cationically polymerizable compositions wherein the cure speeds are surprisingly temperature insensitive. This insensitivity to temperature is more typical of (meth)acrylate photopolymerizable compositions.

The enhancement in the cure speed and cure depth realized by this invention can allow a dentist to prepare and cure larger restorations at one time, thereby saving time and effort. The reduction in unwanted color formation and improved color stability can also make matching the restorative to various tooth shades easier and more accurate over the lifetime of the restorative. The Examples Section describes experiments that quantitatively demonstrate the benefits of the new invention when compared to single-donor restorative formulations.

In addition to use in dental restorative applications, the useful combination of high cure speed, high cure depth, temperature insensitivity and low color formation achievable with this invention in low-stress epoxy resins could find use in other applications. These could include hardcoats for a variety of substrates including various metals, glasses, plastics, papers, wood and the like. Other potential applications include graphic arts imaging (e.g. curable inks), photoresists, solder masks, electronic coatings, photocurable adhesives (e.g. orthodontics) and non-dental photocurable composites (e.g. automotive parts or repair). Other features and advantages of the present invention will be apparent from the following Detailed Description thereof, and from the claims

DETAILED DESCRIPTION

The invention provides a photopolymerizable composition that comprises a cationically polymerizable resin, and a photoinitiator system that contains an iodonium salt, a visible light sensitizer, and an electron donor compound, or a combination of electron donor compounds. The compositions of the invention include one or more anthracene-based compounds as electron donors. In some embodiments, the compositions comprise multiple substituted anthracene compounds or a combination of a substituted anthracene compound with unsubstituted anthracene. The combination of these mixed-anthracene electron donors as part of these photoinitiator systems provides significantly enhanced cure depth and cure speed and temperature insensitivity when compared to comparable single-donor photoinitiator systems in the same matrix. Furthermore, these mixed donor compositions also exhibit the advantages of reduced color formation and improved color stability as compared to many systems comprised of a single electron donor. These features are particularly useful for unfilled and highly filled epoxy-based compositions which exhibit relatively low shrinkage upon polymerization.

Advantageously, the photopolymerizable compositions of the invention are sensitive throughout the "visible light" region and polymerize without appreciable application of heat. The term "visible light" is used throughout this application to refer to light having a wavelength of about 400 to 1000 nanometers (nm). Photopolymerization of the compositions takes place upon exposure of the compositions to a source of actinic radiation having a wavelength within this spectral region.

The cationically polymerizable resins useful in the compositions of the invention include, for example, epoxy (including silicon-containing epoxy), oxetane, spiro-orthocarbonate, and, vinyl ether resins, as well as combinations thereof.

Useful epoxy resins are organic compounds having an oxirane ring, i.e., a group of the formula

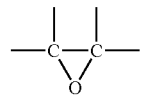

which is polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5, and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy resin by the total number of epoxy-containing molecules present.

These epoxy resins may vary from low molecular weight monomeric materials to high molecular weight polymers and may vary greatly in the nature of their backbone and substituent groups. For example, the backbone may be of any type and substituent groups thereon can be any group that does not substantially interfere with cationic polymerization at room temperature. Illustrative of permissible substituent groups are halogens, ester groups, ethers, sulfonate groups, siloxane groups, nitro groups, phosphate groups, and the like. The molecular weight of the epoxy resin may vary from about 58 to about 100,000 or more.

Particularly preferred epoxy resins include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl)adipate. For a more detailed list of useful epoxides of this nature, reference is made to U.S. Pat. Nos. 3,117,099 and 6,245,828, International Patent Publication No. WO 01/51540, European Patent Publication No. 0 412 430, and Japanese Patent Publication No. 51-033541. Other epoxy resins that are useful in the compositions of this invention include glycidyl ether monomers of the formula

where R' is alkyl or aryl, and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262, and in "Handbook of Epoxy Resins" by Lee and Neville, McGraw-Hill Book Co., New York (1967).

There is a host of commercially available epoxy resins that can be used in this invention. In particular, epoxides that are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp., a subsidiary of Dow Chemical Co.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy)cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$-$C_{10}$ glycidyl ether (e.g., "HELOXY Modifier 7" from Shell Chemical Co.), alkyl $C_{12}$-$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert-butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

Still other useful epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins include epichlorohydrins, alkylene oxides, e.g., propylene oxide, styrene oxide; alkenyl oxides, e.g., butadiene oxide; and glycidyl esters, e.g., ethyl glycidate.

Particularly preferred epoxides are those that contain silicon, useful examples of which are described in International Patent Publication No. WO 01/51540, such as: 7-Oxabicyclo[4.1.0]heptane; 3,3',3'',3'''-[(2,4,6,8-tetramethylcyclotetrasiloxan-2,4,6,8-tetrayl)tetra-2,1-ethandiyl]tetrakis-; 7-Oxabicyclo[4.1.0]heptan, 3,3',3'',3''',3''''-[(2,4,6,8,10-pentamethylcyclopentasiloxan-2,4,6,8,10-pentayl)penta-2,1-ethandiyl]pentakis-, Silane; methylbis[2-(7-oxabicyclo[4.1.0]hept-3-yl)ethyl]phenyl-; Silane, dimethylbis[2-(7-oxabicyclo[4.1.0]hept-3-yl)methyl]-; Silane, dimethyl[2-(7-oxabicyclo[4.1.0]hept-3-yl)methyl][2-(7-oxabicyclo[4.1.0]hept-3-yl)ethyl]-; Silane, 1,4-phenylenbis[dimethyl[2-(7-oxabicyclo[4.1.0]hept-3-yl)ethyl]]-; Silane 1,2-ethylenbis[dimethyl[2-(7-oxabicyclo[4.1.0]hept-3-yl)ethyl]]-; Silane; dimethylbis[2-(7-oxabicyclo[4.1.0]hept-3-yl)ethyl]-; 1,3-Bis[2-(3,4-epoxycyclohexyl)ethyl]-1,1,3,3-tetramethyidisiloxane; Silane 2,5-bicyclo[2.2.1.]heptylenbis[dimethyl[2-(7-oxabicyclo[4.1.0]hept-3-yl)ethyl]]-; Silane 1,6-hexylenbis[dimethyl[2-(7-oxabicyclo[4.1.0]hept-3-yl)ethyl]]-; Silane 1,1',1''-(1,2,4-cyclohexylentris(dimethyl[2-(7-oxabicyclo[4.1.0]hept-3-yl)ethyl]))-; Trisiloxane, 3-[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-3-phenyl-; Disiloxane 1,1',1''-(1,2,4-cyclohexanetriyltri-2,1-ethanediyl)tris[1,1,3,3-tetramethyl-3-[2-(7-oxabicyclo[4.1.0]hept-3-yl)ethyl]]-; Trisiloxane, 3,3-bis[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-; Trisiloxane, 3-[[dimethyl[2-(7-oxabicyclo[4.1.0]hept-3-yl)ethyl]silyl]oxy]-1,1,3,5,5-pentamethyl-1,5-bis[2-(7-oxabicyclo[4.1.0]hept-3-yl)ethyl]-, 1,3,5,7-tetrakis(2,1-ethandiyl-3,4-epoxycyclohexyl)-1,3,5,7-tetramethylcyclotetrasiloxane and 1,3,5,7,9-pentakis(2,1-ethandiyl-3,4-epoxycyclohexyl)-1,3,5,7,9-pentamethylcyclopentasiloxane.

The cationically polymerizable resin may also be provided by a vinyl ether resin. Examples of vinyl ether resins that may be used include, but are not limited to, tri(ethylene glycol) divinyl ether (TEGDVE), glycidyl vinyl ether (GVE), butanediolvinyl ether (BDVE), di(ethylene glycol) divinyl ether (DEGDVE), 1,4-cyclohexanedimethdiol divinyl ether(CHDMDVE), 4-(isopropenyloxymethyl)-1,3-dioxolan-2-one (POMDO), 2-chloroethyl vinyl ether (CEVE), 2-ethylhexyl vinyl ether (EHVE), ethyl vinyl ether (EVE), n-propyl vinyl ether (NPVE), isopropyl vinyl ether (IPVE), n-butyl vinyl ether (NBVE), isobutyl vinyl ether (IBVE), octadecyl vinyl ether (ODVE), cyclohexyl vinyl ether (CVE), butanediol divinyl ether (BDDVE), hydroxybutyl vinyl ether (HBVE), cyclohexanedimethanol monovinyl ether (CHMVE), tert-butyl vinyl ether (TBVE), tert-amyl vinyl ether (TAVE), dodecyl vinyl ether (DDVE), ethylene glycol divinyl ether (EGDVE), ethylene glycol monovinyl ether (EGMVE), hexanediol divinyl ether (HDDVE), hexanediol monovinyl ether (HDMVE), diethylene glycol monovinyl ether (MVE-2), triethyleneglycol methyl vinyl ether (MTGVE), tetraethylene glycol divinyl ether (DVE-4), trimethylolpropane trivinyl ether (TMPTVE), aminopropyl vinyl ether (APVE), polytetrahydrofuran divinyl ether (PTHFDVE), n-butyl vinyl ether (n-BVE), 4-hydroxybutyl vinyl ether (HBVE), ethylene glycol butyl vinyl ether (EGBVE), 2-diethylamino ethyl vinyl ether (DEAEVE), dipropylene glycol divinyl ether (DPGDVE), a vinyl ether terminated aromatic ester monomer (e.g., hydroxybutyl vinyl ether isophthalate which can be purchased from Morflex, Greensboro, N.C. under the trademark VECTOMER 4010), a vinyl ether terminated aliphatic ester monomer (e.g., cyclohexane dimethanol monovinyl ether glutarate which can be purchased from Morflex under the trademark VECTOMER 4020), a vinyl ether terminated aliphatic urethane oligomer (e.g., VECTOMER 2020 which can be purchased from Morflex and a vinyl ether terminated aromatic urethane oligomer (e.g., VECTOMER 2015 and VECTOMER 2010, both of which can be purchased from Morflex).

Blends of various cationically polymerizable resins are also contemplated in this invention. Examples of such blends include two or more weight average molecular weight distributions of resin-containing compounds, such as low molecular weight (below 200), intermediate molecular weight (about 200 to 10,000) and higher molecular weight (above about 10,000). Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

The optional hydroxyl-containing material that may be used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl-containing material can optionally contain other functionalities that do not substantially interfere with cationic polymerization at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl-containing material can, for example, be selected from naturally occurring or synthetically prepared cellulosic materials. Of course, the hydroxyl-containing material is also substantially free of groups that may be thermally or photolytically unstable; that is, the material will not decompose or liberate volatile components at temperatures below about 100° C. or in the presence of actinic light that may be encountered during the desired polymerization conditions for the photocopolymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl) cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.), polytetrahydrofuran with an average molecular weight of 250 (available from Sigma-Aldrich, St. Louis, Mo.), the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230, 0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", "ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl-containing organic material optionally used in the compositions of the invention may vary over broad ranges, depending upon factors such as the compatibility of the hydroxyl-containing material with the resin, the equivalent weight and functionality of the hydroxyl-containing material, the physical properties desired in the final cured composition, the desired speed of photopolymerization, and the like.

Blends of various hydroxyl-containing materials are also contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

If desired, the photopolymerizable composition can also contain a free-radically polymerizable material, including ethylenically unsaturated monomer, monomers or oligomers or polymers. Suitable materials contain at least one ethylenically unsaturated bond, and are capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, the polymerizable material(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

The polymerizable material(s) can also contain hydroxyl and free-radically polymerizable functionalities in a single molecule. Examples of such materials include hydroxyalkylacrylates and hydroxyalkylmethacrylates such as hydroxyethylacrylate, hydroxyethylmethacrylate; glycerol mono- or di-acrylate and methacrylate; and the like.

The cationically polymerizable resin, optional hydroxy-containing material(s), and optional free radically polymerizable material(s) are combined with a multi-component photoinitiator system. The first component in the photoinitiator system is an iodonium salt, e.g., a diaryliodonium salt. The iodonium salt should be soluble in the composition and preferably is shelf-stable, meaning it does not spontaneously promote polymerization when dissolved therein in the presence of the visible light sensitizer and the electron donor compound. Accordingly, selection of a particular iodonium salt may depend to some extent upon the particular resin, visible light sensitizer and electron donor that are chosen. Suitable iodonium salts are described in U.S. Pat. Nos. 3,729,313, 3,741,769, 3,808,006, 4,250,053 and 4,394,403. The iodonium salt can be a simple salt, containing an anion such as $Cl^-$, $Br^-$, $I^-$ or $C_2H_5SO_3^-$; or a metal complex salt containing an antimonate, arsenate, phosphate or borate such as $SbF_5OH^-$ or $AsF_6^-$. Mixtures of iodonium salts can be used if desired.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl) iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl) iodonium hexafluorophosphate; di(4-bromophenyl) iodonium hexafluorophosphate; di(4-methoxyphenyl) iodonium hexafluorophosphate; di(3-carboxyphenyl) iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, and 4-(1-methylethyl)phenyl 4-methylphenyliodonium tetrakis(pentafluorophenyl)borate are among the preferred salts. These salts are preferred because, in general, they promote faster reaction, and are more soluble in inert organic solvents than are other aromatic iodonium salts of complex ions. Combinations of two or more of any of the above salts may also be used.

The aromatic iodonium complex salts may be prepared by metathesis of corresponding aromatic iodonium simple salts (such as, for example, diphenyliodonium bisulfate) in accordance with the teachings of Beringer et al., *J. Am. Chem. Soc.* 81, 342 (1959). Thus, for example, the complex salt diphenyliodonium tetrafluoroborate is prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared in accordance with Beringer et al., above, by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acrylate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0°-5° C. and at room temperature (about 25° C.) for 48 hours and treated with 300 ml of diethyl ether. On concentration, crude diphenyliodonium bisulfate precipitates and may be purified by recrystallization if desired.

Another component in the photoinitiator system is a visible light sensitizer. The visible light sensitizer should be partly or fully soluble in the photopolymerizable composition, free of functionalities that would substantially interfere with the cationic polymerization process, and capable of light absorption somewhere within the range of wavelengths between about 400 and about 1000 nanometers. Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, p-substituted aminostyryl ketone compounds and combinations thereof. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure (e.g., cure of highly-filled composites), it is preferred to employ sensitizers having an extinction coefficient below about 1000 lmole$^{-1}$ cm$^{-1}$, more preferably about or below 100 lmole$^{-1}$ cm$^{-1}$, at the desired wavelength of irradiation for photopolymerization. The alpha-diketones are an example of a class of visible light sensitizers having this property, and are particularly preferred for dental applications. Deep cure can also be achieved utilizing visible light sensitizers with an extinction coefficient greater than 1000 lmole$^{-1}$ cm$^{-1}$, if the sensitizer exhibits a decreasing extinction coefficient upon exposure to light. The xanthene dyes, fluorone dyes, and fluorescein dyes are examples of a class of visible light sensitizers having this property.

By way of example, a preferred class of ketone visible light sensitizers has the formula:

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable l-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'- 3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, 1-phenyl-1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

Another component in the photoinitiator system is an anthracene-based electron donor compound or a combination of such compounds. A variety of anthracene-based compounds can be employed in the photoinitiator systems and generally are capable of increasing the speed of polymerization and/or the depth of polymerization of a composition comprising a cationically polymerizable resin when exposed to visible light of the desired wavelength, as compared to the same composition but excluding the anthracene-based electron donor compound.

More specifically, anthracene-based electron donor compounds conforming to the structure I shown below may be employed.

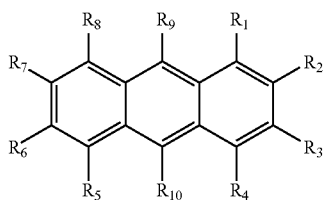

In the above structure I, the substituents $R_1$ to $R_{10}$ may be any group that does not have a substantially adverse effect on cationic polymerization, and are independently selected from H, alkyl groups, aryl groups and/or alkoxy groups, preferably $C_1$-$C_{10}$ alkyl and/or $C_1$-$C_{10}$ alkoxy. The most preferred R-group substituents are methyl, ethyl, propyl, butyl, tert-butyl, methoxy, and ethoxy Particularly useful anthracene-based compounds include: 2-ethyl-9,10-dimethoxyanthracene (EDMOA), 9,10-dimethylanthracene, 9,10-diethoxyanthracene, 1,4-dimethoxyanthracene, 9-methylanthracene, 2-ethylanthracene, 2-tert-butylanthracene, 2,6-di-tert-butylanthracene, 9,10-diphenyl-2,6-di-tert-butylanthracene, and combinations thereof. All of these compounds with the exception of the 2,6-di-tert-butylanthracene derivatives are available from Sigma-Aldrich, St. Louis, Mo.

In one embodiment of the invention, the photoinitiator system comprises a combination of two or more anthracene-based compounds. The mixture may include unsubstituted anthracene (i.e. $R_{1-10}$ are all H), or another anthracene that has a light absorption maximum less than about 400 nanometers, in combination with a substituted anthracene of structure 1, preferably an alkyl or alkoxy substituted anthracene, such as EDMOA, 2,6-di-tert-butylanthracene or 9,10-dimethylanthracene. Alternatively, the system may comprise two or more substituted anthracenes.

Alternatively, many of the preferred anthracene-based compounds disclosed herein exhibit improved performance even when used in the absence of any additional anthracene-based compounds. In particular, alkoxy substituted anthracenes such as 2-ethyl-9,10-dimethoxyanthracene (EDMOA), 9,10-diethoxyanthracene, and 1,4-dimethoxyanthracene when used as the sole electron donor have been shown to possess superior cure speed and/or cure depth compared to previously reported anthracenes. Accordingly, the photoinitiator system may comprise EDMOA, 9,10-diethoxyanthracene, or 1,4-dimethoxyanthracene, either alone or in combination with one or more additional substituted anthracenes, or with unsubstituted anthracene.

The anthracene-based compounds for use in the invention preferably possess one or more (and more preferably several if not all) of the following properties: (a) they are soluble or partially soluble in the polymerizable composition; (b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer; (c) they have an oxidation potential ($E_{ox}$) greater than 0 but less than that of 1,4-dimethoxybenzene when measured versus a saturated calomel electrode (SCE); (d) a $pk_b$ greater than about 8; (e) they impart not more than a minimal amount of objectionable color to the photopolymerized resin; and (f) they cause no more than a minimal amount of polymerization inhibition.

Other factors that may influence the selection of the anthracene-based compound for a particular composition include the cationically polymerizable resin, the iodonium salt, and the visible light sensitizer that have been chosen, as well as the shelf stability of the cationically polymerizable composition.

While preferred anthracene-based compounds for use in the invention have an $E_{ox}$ greater than zero and less than or equal to that of 1,4-dimethoxybenzene, it is more preferred that the electron donor compound have an $E_{ox}$ that is less than about 1.35 volts when measured using a saturated calomel electrode (SCE), and even more preferred that the $E_{ox}$ be between about 0.5 and 1.34 volts (vs. a SCE). $E_{ox}$ values can be measured experimentally, or obtained from established reference sources, such as N. L. Weinburg, Ed., *Technique of Electroorganic Synthesis Part II Techniques of Chemistry*, Vol. V (1975), and C. K. Mann and K. K. Barnes, *Electrochemical Reactions in Nonaqueous Systems* (1970).

Advantageously, the anthracene-based electron donor compound may accelerate the rate of polymerization (as measured by gel time) of the cationically polymerizable resin, as compared to compositions without the electron donor compound. For many uses of the photopolymerizable compositions, the gel time is preferably less than 60 minutes, more preferably less than about 10 minutes, and most preferably less than about 2 minutes as established according to the gel time protocol as reported in U.S. Pat. Application No. 2003/0166737 (Dede et al.). Briefly, the electron donor compound and comparative compounds were evaluated for their effect on the polymerization speed in a particular cationically polymerizable composition by combining the cationically polymerizable resin with the desired visible light sensitizer, iodonium salt, and electron donor compound, and mixing until homogeneous. Each sample was examined for gel time by transferring the photopolymerizable composition to a 6-mm diameter×2.5-mm thick Teflon mold with a polyester film clamped in direct contact with the bottom face. The sample was placed directly beneath the light guide of a VISILUX 2 or ELIPAR Trilight (utilizing the standard light intensity mode for the latter) dental curing light at a distance of 10 mm. Samples were irradiated up to a maximum of 120 seconds and hard gel times were established by probing the surface with a plastic probe until a hard, tack free surface was observed.

The individual components of the photoinitiator system are provided in photopolymerizingly effective amounts (i.e., amounts effective to yield a photoinitiator system that can initiate photopolymerization of the cationically polymerizable resin or, more preferably, that can accelerate the rate of polymerization). Preferably, the visible light sensitizer is present at about 0.05-5.0 weight percent based on the overall photopolymerizable composition, more preferably, at about 0.10-2.0 weight percent. The iodonium salt is preferably present at about 0.05-10.0 weight percent, more preferably at about 0.10-5.0 weight percent, and most preferably at about 0.50-3.0 weight percent, based on the overall composition. The electron donor compound or compounds (i.e. anthracenes) are preferably present at about 0.01-5.0 weight percent, more preferably about 0.05-1.0 weight percent, and most preferably about 0.05-0.50 weight percent, based on the overall composition.

The photopolymerizable compositions of the invention are prepared by simply admixing, under "safe light" conditions, the components of the inventive compositions. Suitable inert solvents may be employed if desired when effecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The compositions of the present invention provide a very useful combination of polymerization speed, polymerization depth, and shelf life. They polymerize well even when loaded with large amounts of filler, and can be used in a variety of applications including hardcoats for a variety of substrates including various metals, glasses, plastics, papers, wood and the like. Other potential applications include graphic arts imaging (e.g., for color proofing systems, curable inks, or silverless imaging), printing plates (e.g., projection plates or laser plates), photoresists, solder masks, electronic conformal coatings and underfills, optical fiber coatings, coated abrasives, magnetic media, photocurable adhesives (e.g. for orthodontic, electronic, fiber optic and medical applications etc.), hardcoats (e.g., for optical lenses), and photocurable composites (e.g., for autobody repair or dentistry). Dental, electronics, optical lenses, and optical fiber applications particularly benefit from the unique compositions of the present invention.

Acrylate- and methacrylate-based materials have been commonly used for adhesive and restorative dental compositions. These materials offer the advantage of being polymerizable with visible light using photoinitiator systems, but have the disadvantage of undergoing a relatively high degree of shrinkage during the polymerization process. In contrast, the cationically polymerizable resins found in the compositions of the present invention shrink significantly less than acrylate or methacrylate resins during polymerization. The present invention provides a system for polymerizing cationically polymerizable resins in an acceptable time frame, e.g., less than 120 seconds, and to a sufficient depth using visible light source equipment already available in the dental office or electronics fabrication facilities.

The compositions of the invention are particularly well adapted for use as a wide variety of dental materials, which may be filled or unfilled. Such dental materials include direct esthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

In certain dental applications, the use of a filler may be appropriate. The choice of the filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Cationically polymerizable compositions of the invention can be prepared with refractive indices which approach or approximate the refractive indices of fillers such as quartz (refractive index 1.55), submicron silica (refractive index 1.46), and 5.5:1 mole ratio SiO:ZrO, non-vitreous microparticles (refractive index 1.54). In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926 B1.

The amount of filler which is incorporated into the composite, referred to herein as the "loading level" and expressed as a weight percent based on the total weight of the dental material, will vary depending on the type of filler, the cationically curable resin and other components of the composition, and the end use of the composite.

For some dental materials, such as sealants, the cationically polymerizable compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 60 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter of less than about 50 micrometers and an average particle diameter of less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or nonradiopaque.

Examples of suitable inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. Examples of coupling agents include silanes such as gamma-methacryloxypropyltrimethoxysilane, gamma-mercaptopropyltriethoxysilane, beta-(3,4-epoxycyclohexyl)ethyltrimethoxysilane, gamma-glycidoxypropyltrimethoxysilane, and the like.

The materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on previous experience with dental materials. When the dental material is applied to a tooth, the tooth can optionally be pre-treated with a primer and/or an adhesive by methods known to those skilled in the art.

Although the features and advantages of this invention are illustrated by the following examples, the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Cure Speed and Enthalpy Test Method A

Test samples were evaluated for cure speed and enthalpy with a 2920 Differential Scanning Photocalorimeter (TA Instruments, New Castle Del.). Samples (10 mg) in open aluminum pans were exposed to low-intensity visible light (3 mW/cm$^2$, 400-800 nm) under nitrogen gas purge and the Photocalorimeter measured the amount of heat flow necessary to maintain isothermal conditions (37° C.) as the polymerization reaction occurred. A dual sample cell was used in which two samples were run simultaneously against a cured reference sample. Induction times, reaction peak (Peakmax) times, and total reaction enthalpy were measured. Results were reported as the average of two replicates.

Cure Speed and Enthalpy Test Method B

Cure speed and enthalpy were analyzed as described in the Cure Speed and Enthalpy Test Method A, except that the sample size was 25 mg and the Photocalorimeter measured the amount of heat flow necessary to maintain isothermal conditions at several temperatures (25° C., 37° C. and 45° C.) as the polymerization reaction occurred. The sample was held isothermally for 5 minutes and then the light was turned on for an exposure time of 60 minutes. Results were reported as the average of four replicates.

Gel Time Test Method

Gel times were determined for samples applied to either a polyester film or a sheet of cold-rolled steel according to the following procedure. The samples were smeared onto the film or steel sheet surface with a plastic mixing stick to a thickness of about 0.5 to 1.0 mm. A 380 mW/cm$^2$ curing light (ELIPAR Trilight, 3M ESPE Company, St. Paul, Minn.) was held 1 cm above the smeared samples and used to irradiate the samples until they gelled. The gel time of the samples was measured with a stopwatch and was defined as either when the sample visually showed a significant change in refractive index and reflection and/or when the sample became hard as determined by gentle tapping with the mixing stick. Results were reported as the average of at least 3 replicates.

Depth of Cure Test Method A

Depth of cure (i.e., cure depth) was analyzed by packing a paste sample into a cylindrical opaque plastic curing mold (11-mm deep, 4-mm diameter) and curing the sample for 40 seconds with a 900 mW/cm$^2$ curing light (XL3000, 3M ESPE Company). The cured sample was removed from the mold and uncured paste was scraped off of the sample with a plastic applicator after about one minute of curing. Results were reported as the average of four replicates.

Depth of Cure Test Method B

Depth of cure (i.e., cure depth) was analyzed as described in the Depth of Cure Test Method A, except that the curing mold was 12-mm deep and the curing light was an ELIPAR Trilight Standard (800 mW/cm$^2$) (3M ESPE Company).

Color Formation and Stability Test Method A

Color formation and color stability were determined according to the following procedure. A test sample paste was pressed into a 1-mm thick mold (30-mm diameter) and irradiated for 120 seconds with a broad spectrum white light and for 160 seconds with a 900 mW/cm$^2$ curing light (XL3000, 3M ESPE Company). The resulting cured disk was analyzed on an Ultrascan XE Color Analyzer (Hunter Associates Laboratory, Reston Va.). Results were reported as color values on the L* a* b* scale and as Delta E values (representing changes in color) after a 1-day period in which the cured disk was aged in water at 37° C. The b* values (the amount of yellow coloration) and the Delta E values (color stability) are particularly important values to monitor for aesthetically pleasing anterior dental restorative applications. Low b* values (below about 20) allow compositions to be formulated that match the lightest shades on the Vita shade guide, while low Delta E values indicate good color stability and the ability of the restorative to hold the shade match over time.

Color Formation and Stability Test Method B

Color formation and color stability were determined as described in the Color Formation and Stability Test Method A, except that the curing mold was 1-mm thick and 15-mm in diameter, the curing light was an ELIPAR Trilight Standard (800 mW/cm$^2$) (3M ESPE Company), and the color analyzer was a Hunter Lab Scan 045.

Abbreviations, Descriptions, and Sources of Materials

| Name or Abbreviation | Description and Source of Material |
| --- | --- |
| TMOB | 1,2,4-Trimethoxybenzene (Sigma-Aldrich, St. Louis, MO) |
| Anthracene | Anthracene (Sigma-Aldrich) |
| EDMOA | 2-Ethyl-9,10-dimethoxyanthracene (Sigma-Aldrich) |
| DMOA | 1,4-Dimethoxyanthracene (Sigma-Aldrich) |
| DMA | 9,10-Dimethylanthracene (Sigma-Aldrich) |
| DEOA | 9,10-Diethoxyanthracene (Sigma-Aldrich) |
| MA | 9-Methylanthracene (Sigma-Aldrich) |
| EA | 2-Ethylanthracene (Sigma-Aldrich) |
| DBA | 2,6-Di-tert-butylanthracene (Prepared according to the general procedure described in J. org. Chem. 1977, 42(14), pp 2407-2410. Starting materials: anthracene + tert-butanol/trifluoroacetic acid) |
| DPDBA | 9,10-Diphenyl-2,6-di-tert-butylanthracene (Prepared according to the general procedure described in J. org. Chem. 1977, 42(14), pp 2407-2410. Starting materials: 9,10-diphenylanthracene + tert-butanol/trifluoroacetic acid) |
| EDMAB | Ethyl 4-(N,N-dimethylamino)benzoate (Sigma-Aldrich) |
| CPQ | Camphorquinone (Sigma-Aldrich) |
| RHODORSIL 2074 | 4-Methylphenyl-4-isopropyliphenyliodonium tetrakis(pentafluorophenyl)borate (Rhone-Poulenc, France) |
| TINUVIN 292 | Bis(1,2,2,6,6-pentamethyl-4-piperidinyl) sebacate (Ciba Specialty Chemicals, Tarrytown, NY) |
| TINUVIN 328 | 2-(2-Hydroxy-3,5-di-tert-amylphenyl) benzotriazole (Ciba) |
| LUMILUX Blue | Diethyl-2,5-dihydroxyterephthalate (Honeywell Seelze, Germany) |
| CYGEPSI Resin | Silorane epoxy material; a 50-50 weight percent mixture of the following two components: silane, methylbis[2-(7-oxabicyclo-[4.1.0]hept-3-yl)ethyl]phenyl and 1,3,5,7-tetrakis(1,2-ethanediyl-3,4-epoxycyclohexyl)-1,3,5,7-tetramethylcyclotetrasiloxane; as described for "Monomer Composition 2" in U.S. Patent Application No. 2003/0035899 (Klettke et al.), except that the ratio of components in CYGEPSI Resin was 50-50 weight percent. |
| Poly-THF | Polytetrahydrofuran (Sigma-Aldrich) |
| Pyridinium Tosylate | Pyridinium p-toluenesulfonate (Sigma-Aldrich) |
| Filler A | Silane-treated quartz filler [Prepared by silane treating quartz (Quarzwerke GmbH, Frechen, Germany) with 3-glycidyloxypropyl-trimethoxysilane (ABCR GmbH, Karlsruhe, Germany) at a level of 5% by weight using standard silane-treatment procedures.] |

Examples 1-16 and Comparative Examples C1-C7

Resin Compositions Containing Substituted Anthracene Derivatives

A Stock Resin Composition (SRC-1) was prepared by combining CYGEPSI Resin (185.7 g), CPQ (1.00 g), RHODORSIL 2074 (5.97 g), poly-THF (6.03 g), Pyridinium Tosylate (0.08 g), TINUVIN 292 (0.09 g), TINUVIN 328 (0.73 g), and LUMILUX Blue (0.03 g). A variety of electron donors, including no electron donor (Control; C1); EDMAB, anthracene, alkyl- and phenyl-substituted anthracenes (Comparative Examples C2-C7); alkoxy-substituted anthracenes (Examples 1-3); and combinations of substituted anthracenes with anthracene (Examples 4-16) were added to SRC-1 and the resulting compositions evaluated with respect to reaction cure speed and enthalpy according to the Cure Speed and Enthalpy Test Method A described herein. The concentration of electron donors in SRC-1 and the evaluation results are provided in Table 1A. The electron donors used alone were added to SRC-1 in equimolar amounts, whereas the electron donors used in combination were added to SRC-1 in varying amounts as shown in Table 1A.

The compositions described above (Comparative Examples C1-C7 and Examples 1-3, 9, and 12-16) were also evaluated for gel time on polyester film and on cold-rolled steel sheeting according to the Gel Time Test Method described herein. The concentration of electron donors in SRC-1 and the evaluation results are provided in Table 1B.

TABLE 1A

| | | | Cure Speed and Enthalpy | | |
| --- | --- | --- | --- | --- | --- |
| Ex. | Electron Donor | Concentration In SRC-1 (ppm) | Induction Time (sec) | Peakmax Time (sec) | Enthalpy (J/g) |
| C1 | None | 0 | 226 | 395 | 201.2 |
| C2 | EDMAB | 1483 | 56 | 109 | 130.7 |
| C3 | TMOB | 1717 | 203 | 316 | 208.0 |
| C4 | Anthracene | 1500 | 147 | 210 | 223.2 |

TABLE 1A-continued

| | | | Cure Speed and Enthalpy | | |
|---|---|---|---|---|---|
| Ex. | Electron Donor | Concentration In SRC-1 (ppm) | Induction Time (sec) | Peakmax Time (sec) | Enthalpy (J/g) |
| C5 | DMA | 1300 | 65 | 100 | 261.6 |
| C6 | MA | 1383 | 92 | 142 | 244.0 |
| C7 | EA | 1300 | 121 | 176 | 236.[2 |
| 1 | EDMOA | 1000 | 67 | 98 | 241.5 |
| 2 | DMOA | 1117 | 38 | 63 | 303.3 |
| 3 | DEOA | 1000 | 60 | 95 | 254.5 |
| 4 | EDMOA/Anthracene | 250/1500 | 78 | 134 | 241.7 |
| 5 | EDMOA/Anthracene | 500/1500 | 63 | 94 | 256.2 |
| 6 | EDMOA/Anthracene | 750/1500 | 53 | 85 | 272.2 |
| 7 | EDMOA/Anthracene | 1000/1500 | 59 | 91 | 290.7 |
| 8 | EDMOA/Anthracene | 250/500 | 73 | 108 | 237.5 |
| 9 | EDMOA/Anthracene | 500/500 | 64 | 96 | 255.9 |
| 10 | EDMOA/Anthracene | 750/500 | 52 | 91 | 283.5 |
| 11 | EDMOA/Anthracene | 1000/500 | 59 | 90 | 262.3 |
| 12 | DMOA/Anthracene | 550/500 | 49 | 72 | 270.4 |
| 13 | DMA/Anthracene | 650/500 | 63 | 107 | 282.9 |
| 14 | DEOA/Anthracene | 500/500 | 65 | 95 | 254.0 |
| 15 | MA/Anthracene | 700/500 | 102 | 143 | 238.7 |
| 16 | EA/Anthracene | 650/500 | 100 | 201 | 229.4 |

It is observed from Table 1A that compositions containing the alkoxy-substituted anthracenes used alone (Examples 1-3) and compositions containing mixtures of unsubstituted anthracene plus a substituted anthracene (Examples 4-16) all provided cure speeds and/or enthalpy values greater than the composition containing unsubstituted anthracene alone (Comparative Example C4) or any other of the comparative examples (C1-C7).

Compositions containing mixtures of anthracene plus an alkyl-substituted anthracene (Examples 13, 15-16) all provided cure speeds greater than would be predicted based on the cure speeds of the compositions containing an alkyl-substituted anthracene alone (Comparative Examples C5-C7) or anthracene alone (Comparative Example C4).

The alkoxy-substituted anthracenes used alone and compositions containing mixtures of anthracene plus a substituted anthracene generally had higher enthalpy numbers and cure speeds (based on peak max) than anthracene or other comparative electron donors alone.

TABLE 1B

| | | | Gel Time (seconds) | |
|---|---|---|---|---|
| Ex. | Electron Donor | Concentration In SRC-1 (ppm) | Polyester Film | Steel Sheet |
| C1 | None | 0 | 28 | 50 |
| C2 | EDMAB | 1483 | 6 | 12 |
| C3 | TMOB | 1717 | 18 | 28 |
| C4 | Anthracene | 1500 | 15 | 23 |
| C5 | DMA | 1300 | 6 | 7 |
| C6 | MA | 1383 | 7 | 9 |
| C7 | EA | 1300 | 8 | 12 |
| 1 | EDMOA | 1000 | 6 | 8 |
| 2 | DMOA | 1117 | 4 | 6 |
| 3 | DEOA | 1000 | 5 | 8 |
| 9 | EDMOA/Anthracene | 500/500 | 6 | 7 |
| 12 | DMOA/Anthracene | 550/500 | 4 | 5 |
| 13 | DMA/Anthracene | 650/500 | 6 | 8 |
| 14 | DEOA/Anthracene | 500/500 | 7 | 8 |
| 15 | MA/Anthracene | 700/500 | 8 | 9 |
| 16 | EA/Anthracene | 650/500 | 8 | 10 |

It is observed from Table 1B that compositions containing the alkoxy-substituted anthracenes used alone (Examples 1-3) and compositions containing mixtures of unsubstituted anthracene plus a substituted anthracene (Examples 9, 12-16) all provided gel times faster than the composition containing anthracene alone (Comparative Example C4). The fastest gel times were observed with certain alkoxy-substituted anthracenes used alone and with certain combinations of alkoxy-substituted anthracenes with unsubstituted anthracene.

Examples 1R-16R and Comparative Examples C1R-C7R

Filled Compositions Containing Substituted Anthracene Derivatives

The resin compositions containing various electron donors and mixtures of electron donors (Examples 1-16 and Comparative Examples C1-C7) were converted to filled compositions by the addition of 70% by weight Filler A. The resulting filled compositions (Examples 1R-16R and Comparative Examples C1R-C7R) could be characterized, for example, as restorative pastes and were evaluated for reaction cure speed and enthalpy and for depth of cure according to the Cure Speed and Enthalpy Test Method A and the Depth of Cure Test Method A provided herein. The evaluation results are provided in Table 2. The samples were also evaluated for color formation and color stability according to the Color Formation and Stability Test Method A provided herein and evaluation results are provided in Table 3.

TABLE 2

| Ex. | Electron Donor | Cure Depth (mm) | Cure Speed and Enthalpy | | |
|---|---|---|---|---|---|
| | | | Induction Time (sec) | Peakmax Time (sec) | Enthalpy (J/g) |
| C1R | None | 3.91 | 273 | 546 | 52.8 |
| C2R | EDMAB | 8.33 | 59 | 110 | 53.8 |
| C3R | TMOB | 5.33 | 202 | 369 | 58.8 |
| C4R | Anthracene | 6.84 | 140 | 249 | 68.6 |
| C5R | DMA | 8.33 | 52 | 102 | 68.7 |
| C6R | MA | 7.78 | 82 | 160 | 67.8 |
| C7R | EA | 7.38 | 93 | 165 | 67.0 |
| 1R | EDMOA | 8.09 | 45 | 104 | 82.2 |
| 2R | DMOA | 6.65 | 30 | 68 | 68.4 |
| 3R | DEOA | 8.16 | 44 | 92 | 70.3 |
| 4R | EDMOA/Anthracene | 6.69 | 62 | 178 | 67.1 |
| 5R | EDMOA/Anthracene | 9.01 | 49 | 98 | 72.2 |
| 6R | EDMOA/Anthracene | 9.00 | 43 | 82 | 73.8 |
| 7R | EDMOA/Anthracene | 8.89 | 42 | 83 | 76.1 |
| 8R | EDMOA/Anthracene | 8.02 | 61 | 116 | 69.5 |
| 9R | EDMOA/Anthracene | 9.13 | 49 | 97 | 72.3 |
| 10R | EDMOA/Anthracene | 9.06 | 51 | 92 | 74.0 |
| 11R | EDMOA/Anthracene | 8.88 | 44 | 85 | 74.0 |
| 12R | DMOA/Anthracene | 7.43 | 37 | 72 | 69.0 |
| 13R | DMA/Anthracene | 8.58 | 59 | 105 | 70.6 |
| 14R | DEOA/Anthracene | 8.83 | 53 | 100 | 70.0 |
| 15R | MA/Anthracene | 8.01 | 89 | 147 | 71.0 |
| 16R | EA/Anthracene | 7.36 | 120 | 204 | 71.3 |

It is observed from Table 2 that the cure speed and enthalpy trends were much the same as those observed in Table 1. The overall enthalpy values were significantly lower due to the presence of the inert inorganic quartz filler present in the filled compositions at 70% by weight. Table 2 shows that filled compositions containing the alkoxy-substituted anthracenes used alone (Examples 1R-3R) provided cure speeds greater than all of the comparative electron donors alone (C1R-C7R). In addition, the filled compositions containing mixtures of unsubstituted anthracene plus a substituted anthracene (Examples 4R-16R) all provided cure speeds greater than the filled composition containing anthracene alone (Comparative Example C4R). Additionally, Examples 1R, 3R, and 5R-16R all provided cure depths greater than the Comparative Example C4R.

TABLE 3

| Example | Electron Donor | L* | A* | b* | Delta E (1 Day) |
|---|---|---|---|---|---|
| C1R | None | 91.18 | −1.95 | 6.84 | 1.91 |
| C2R | EDMAB | 90.62 | −5.87 | 16.80 | 3.93 |
| C3R | TMOB | 90.39 | −1.81 | 8.39 | 2.60 |
| C4R | Anthracene | 88.60 | −3.68 | 11.55 | 3.37 |
| C5R | DMA | 83.66 | −5.53 | 16.66 | 9.71 |
| C6R | MA | 85.76 | −4.35 | 13.86 | 6.46 |
| C7R | EA | 87.20 | −2.88 | 11.79 | 4.32 |
| 1R | EDMOA | 82.87 | −2.73 | 19.80 | 7.41 |
| 2R | DMOA | 68.83 | 0.34 | 21.29 | 20.60 |
| 3R | DEOA | 83.01 | −2.63 | 19.99 | 9.13 |
| 4R | EDMOA/Anthracene | 87.64 | −3.30 | 13.41 | 4.19 |
| 5R | EDMOA/Anthracene | 86.43 | −4.16 | 17.31 | 5.04 |
| 6R | EDMOA/Anthracene | 83.89 | −3.45 | 20.18 | 6.33 |
| 7R | EDMOA/Anthracene | 82.81 | −2.76 | 20.64 | 7.23 |
| 8R | EDMOA/Anthracene | 88.29 | −3.53 | 12.86 | 3.77 |
| 9R | EDMOA/Anthracene | 87.10 | −4.33 | 16.72 | 4.29 |
| 10R | EDMOA/Anthracene | 85.09 | −3.82 | 19.13 | 5.70 |
| 11R | EDMOA/Anthracene | 83.10 | −2.90 | 20.00 | 7.35 |
| 12R | DMOA/Anthracene | 78.79 | −2.05 | 21.66 | 12.23 |
| 13R | DMA/Anthracene | 86.05 | −6.16 | 18.19 | 6.60 |
| 14R | DEOA/Anthracene | 87.28 | −4.59 | 16.73 | 4.75 |
| 15R | MA/Anthracene | 86.49 | −4.33 | 14.80 | 4.42 |
| 16R | EA/Anthracene | 87.87 | −3.00 | 12.58 | 3.24 |

It is observed from Table 3 that each filled composition containing a substituted anthracene (Examples 1R-3R and Comparative Examples C5R-C7R) had a greater amount of color (based on b* values) and less color stability (based on Delta E values) than the composition containing only anthracene (Comparative Example C4R). Compositions containing DMOA, alone or in combination, (Examples 2R and 12R) showed the greatest amount of color (b* values) and least color stability (Delta E). Some of the filled compositions containing a mixture of anthracene with a substituted anthracene (e.g., Examples 4R, 5R, 8R-10R, and 14R) showed lower color (b* values) and greater color stability (Delta E) than the corresponding substituted anthracene used alone. Several of the filled compositions containing a mixture of anthracene with a substituted anthracene exhibited initial color and color stability (e.g., examples 8R, 15R, and 16R) similar to anthracene alone.

Examples 17R-24R and Comparative Examples C8R-C14R

Filled Compositions Containing Substituted Anthracene Derivatives

In a separate series of experiments, a variety of electron donors, including anthracene and dialkyl-substituted anthracenes (Comparative Examples C8R-C14R); alkoxy-substituted anthracenes (Examples 17R-18R); and combinations of substituted anthracenes with anthracene or with other substituted anthracenes (Examples 19R-24R) were added to the resin SRC-1 and the resulting compositions converted to filled compositions by the addition of 70% by weight Filler A. The resulting filled compositions (i.e., restorative pastes) were evaluated for depth of cure according to the Depth of Cure Test Method B described herein and for color formation and color stability according to the Color Formation and Stability Test Method B provided herein. The concentration of electron donors in SRC-1 for the filled compositions and the evaluation results are provided in Table 4.

TABLE 4

| Ex. | Electron Donor | Concentration in SRC-1 (ppm) | Cure Depth (mm) | L* | a* | b* | Delta E (1 Day) |
|---|---|---|---|---|---|---|---|
| C8R | Anthracene | 1000 | 7.14 | 78.61 | −5.36 | 12.68 | 4.75 |
| C9R | DMA | 500 | 8.04 | 77.45 | −6.49 | 17.35 | 6.11 |
| C10R | DMA | 1000 | 8.03 | 75.23 | −6.74 | 20.33 | 8.42 |
| C11R | DBA | 500 | 7.87 | 78.94 | −4.89 | 11.12 | 4.39 |
| C12R | DBA | 1000 | 8.35 | 78.74 | −4.63 | 11.87 | 4.63 |
| C13R | DPDBA | 1000 | 7.85 | 79.84 | −7.38 | 14.54 | 3.41 |
| C14R | DPDBA | 2000 | 8.35 | 79.10 | −7.39 | 15.07 | 3.78 |
| 17R | EDMOA | 500 | 7.97 | 78.20 | −5.42 | 16.24 | 4.02 |
| 18R | EDMOA | 1000 | 8.69 | 75.63 | −5.25 | 20.22 | 5.60 |
| 19R | EDMOA/Anthracene | 500/500 | 8.93 | 77.44 | −5.27 | 15.21 | 4.51 |
| 20R | EDMOA/DBA | 500/500 | 8.99 | 76.93 | −5.64 | 17.86 | 4.94 |
| 21R | DMA/Anthracene | 500/500 | 8.22 | 76.95 | −6.37 | 17.87 | 6.74 |
| 22R | DMA/DBA | 500/500 | 8.03 | 76.75 | −6.37 | 18.18 | 6.75 |
| 23R | DBA/Anthracene | 500/500 | 7.62 | 75.61 | −4.89 | 13.31 | 6.74 |
| 24R | DPDBA/Anthracene | 1000/500 | 7.88 | 77.42 | −7.05 | 16.27 | 4.67 |

Table 4 shows that filled compositions containing the alkoxy-substituted anthracenes used alone (Examples 17R-18R) and filled compositions containing mixtures of a substituted anthracene plus anthracene or plus another substituted anthracene (Examples 19R-24R) all provided cure depths greater than the filled composition containing anthracene alone (Comparative Example C8R).

Examples 25R-26R and Comparative Example C15R

Filled Compositions Containing Anthracene, EDMOA, or Anthracene plus EDMOA

Filled compositions were prepared as described for Examples 1R-16R and Comparative Examples C1R-C7R, except that the compositions included a resin system containing SRC-1 and either 1000 ppm anthracene (Comparative Example C15R), 1000 ppm EDMOA (Example 25R), or 1000 ppm anthracene plus 500 ppm EDMOA (Example 26R). The three compositions were evaluated for reaction cure speed and enthalpy at 25° C., 37° C., and 45° C. according to the Cure Speed and Enthalpy Test Method B described herein and the results are reported in Table 5.

TABLE 5

| | | | Cure Speed and Enthalpy | | |
|---|---|---|---|---|---|
| Ex. | Electron Donor | Temperature (° C.) | Induction Time (sec) | Peakmax Time (sec) | Enthalpy (J/g) |
| C15R | Anthracene | 25 | 259 | 397 | 58.2 |
| 25R | EDMOA | 25 | 63 | 111 | 65.1 |
| 26R | EDMOA/Anthracene | 25 | 64 | 114 | 62.5 |
| C15R | Anthracene | 37 | 185 | 272 | 67.1 |
| 25R | EDMOA | 37 | 53 | 95 | 72.9 |
| 26R | EDMOA/Anthracene | 37 | 52 | 91 | 70.6 |
| C15R | Anthracene | 45 | 154 | 218 | 69.5 |
| 25R | EDMOA | 45 | 49 | 83 | 77.2 |
| 26R | EDMOA/Anthracene | 45 | 48 | 82 | 75.9 |

The data of Table 5 show that the compositions containing either EDMOA alone (Example 25R) or the mixed anthracenes (Example 26R) had significantly greater cure speeds and were significantly less impacted by temperature variation as compared to the composition containing only anthracene (Comparative Example C15R). The mixed anthracene system and EDMOA alone had similar cure speeds at each temperature tested. The data of Table 5 also show that the compositions containing either EDMOA alone (Example 25R) or the mixed anthracenes (Example 26R) had significantly greater enthalpies compared to the composition containing only anthracene alone for a specified temperature.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

We claim:
1. A photoinitiator system comprising:
(a) an iodonium salt;
(b) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof;
(c) a first anthracene that has a light absorption maximum less than about 400 nanometers; and
(d) a second anthracene having the following structure

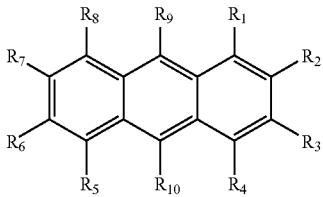

wherein each of $R_1$ to $R_{10}$ is independently selected from H, or alkyl, phenyl or alkoxy groups, provided that at least one of $R_1$ to $R_{10}$ is not H.

2. A photopolymerizable composition comprising:
(a) a cationically polymerizable resin; and
(b) a photoinitiator system for the cationically polymerizable resin, the photoinitiator system comprising:
(i) an iodonium salt;
(ii) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof;
(iii) a first anthracene that has a light absorption maximum less than about 400 nanometers; and
(iv) a second anthracene having the following structure

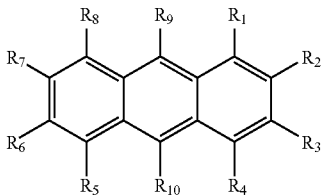

wherein each of $R_1$ to $R_{10}$ is independently selected from H, alkyl, phenyl or alkoxy groups, provided that at least one of $R_1$ to $R_{10}$ is not H.

3. The photopolymerizable composition according to claim 2, wherein the cationically polymerizable resin is selected from the group consisting of epoxy, oxetane, vinyl ether and spiro-orthocarbonate resins, and combinations thereof.

4. The photopolymerizable composition according to claim 3, wherein the cationically polymerizable resin comprises an epoxy resin.

5. The photopolymerizable composition according to claim 4, wherein the cationically polymerizable resin comprises a silicon-containing epoxy resin.

6. The photopolymerizable composition according to claim 3, wherein the cationically polymerizable resin comprises a blend of a silicon-containing epoxy resin and an epoxy resin that does not contain silicon.

7. The photopolymerizable composition according to claim 2, wherein the iodonium salt is selected from the group consisting of diaryliodonium hexafluorophosphate, diaryliodonium hexafluoroantimonate, diaryliodonium tetrakis (pentafluorophenyl)borate, 4-octyloxyphenyl phenyliodonium hexafluoroantimonate, 4-(2-hydroxytetradecyloxyphenyl)phenyliodonium hexafluoroantimonate, 4-(1-methylethyl)phenyl 4-methylphenyliodonium tetrakis(pentafluorophenyl)borate, and combinations thereof.

8. The photopolymerizable composition according to claim 2, wherein the visible light sensitizer is an alpha-diketone.

9. The photopolymerizable composition according to claim 8, wherein said alpha-diketone is camphorquinone.

10. The photopolymerizable composition according to claim 2, wherein the first anthracene is unsubstituted anthracene.

11. The photopolymerizable composition according to claim 2, wherein the second anthracene is selected from 2-ethyl-9,10-dimethoxyanthracene, 9,10-dimethylanthracene, 9,10-diethoxyanthracene, 1,4-dimethoxyanthracene, 9-methylanthracene, 2-ethylanthracene, 1,4-dimethoxyanthracene, 2-tert-butylanthracene, 2,6-di-tert-butylanthracene, and 9,10-diphenyl-2,6-di-tert-butylanthracene.

12. The photopolymerizable composition according to claim 2, wherein the second anthracene is 2-ethyl-9,10-dimethoxyanthracene.

13. The photopolymerizable composition according to claim 2, wherein the second anthracene is 9,10-dimethylanthracene.

14. The photopolymerizable composition according to claim 2, wherein the second anthracene is 9,10-diethoxyanthracene.

15. The photopolymerizable composition according to claim 2, wherein the second anthracene is 1,4-dimethoxyanthracene.

16. The photopolymerizable composition according to claim 2, wherein the second anthracene is 9-methylanthracene.

17. The photopolymerizable composition according to claim 2, wherein the second anthracene is 2-ethylanthracene.

18. The photopolymerizable composition according to claim 2, wherein at least one of $R_1$ to $R_{10}$ is tert-butyl.

19. The photopolymerizable composition according to claim 2, wherein the second anthracene is 2,6-di-tert-butylanthracene.

20. The photopolymerizable composition according to claim 2, further comprising a free-radically polymerizable resin.

21. The photopolymerizable composition according to claim 2, further comprising a hydroxyl-containing material.

22. The photopolymerizable composition according to claim 2, wherein the photopolymerizable composition is a photopolymerizable adhesive.

23. A photoinitiator system comprising:
(a) an iodonium salt;
(b) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof;
(c) an electron donor comprising an alkoxy substituted anthracene; and
(d) a second electron donor compound having the following formula:

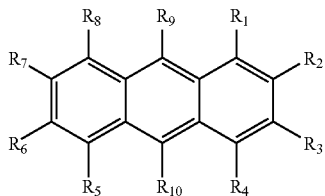

wherein each of $R_1$ to $R_{10}$ is independently selected from H, alkyl, phenyl or alkoxy groups.

24. A photopolymerizable composition comprising:
(a) a cationically polymerizable resin; and
(b) a photoinitiator system for the cationically polymerizable resin, the photoinitiator system comprising:
  (i) an iodonium salt;
  (ii) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof;
  (iii) an electron donor comprising an alkoxy substituted anthracene; and
  (iv) a second electron donor having the following formula:

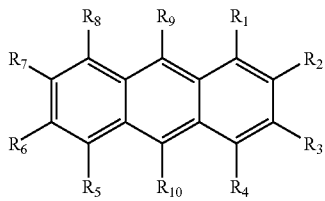

wherein each of $R_1$ to $R_{10}$ is independently selected from H, alkyl, phenyl or alkoxy groups.

25. The photopolymerizable composition according to claim 24, wherein the cationically polymerizable resin is selected from the group consisting of epoxy, oxetane, vinyl ether and spiro-orthocarbonate resins, and combinations thereof.

26. The photopolymerizable composition according to claim 25, wherein the cationically polymerizable resin comprises an epoxy resin.

27. The photopolymerizable composition according to claim 26, wherein the cationically polymerizable resin comprises a silicon-containing epoxy resin.

28. The photopolymerizable composition according to claim 25, wherein the cationically polymerizable resin comprises a blend of a silicon-containing epoxy resin and an epoxy resin that does not contain silicon.

29. The photopolymerizable composition according to claim 24, wherein the iodonium salt is selected from the group consisting of diaryliodonium hexafluorophosphate, diaryliodonium hexafluoroantimonate, diaryliodonium tetrakis(pentafluorophenyl)borate, 4-octyloxyphenyl phenyliodonium hexafluoroantimonate, 4-(2-hydroxytetradecyloxyphenyl) phenyliodonium hexafluoroantimonate, 4-(1-methylethyl)phenyl 4-methylphenyliodonium tetrakis(pentafluorophenyl)borate, and combinations thereof.

30. The photopolymerizable composition according to claim 24, wherein the visible light sensitizer is an alpha-diketone.

31. The photopolymerizable composition according to claim 30, wherein the alpha-diketone is camphorquinone.

32. The photopolymerizable composition according to claim 24, wherein the alkoxy substituted anthracene is selected from 2-ethyl-9,10-dimethoxyanthracene, 9,10-dimethoxyanthracene, 9,10-diethoxyanthracene, and 1,4-dimethoxyanthracene.

33. A photoinitiator system comprising:
(a) an iodonium salt;
(b) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof;
(c) a first anthracene and a second anthracene both having the following structure:

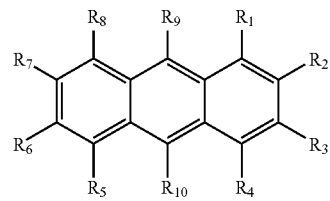

wherein for said first anthracene each of $R_1$ to $R_{10}$ is independently selected from H, alkyl, phenyl, or alkoxy groups, provided that at least one of $R_1$ to $R_{10}$ is alkoxy, and
wherein for said second anthracene each of $R_1$ to $R_{10}$ is independently selected from H, alkyl, phenyl or alkoxy groups.

34. A photopolymerizable composition comprising:
(a) a cationically polymerizable resin; and
(b) a photoinitiator system for the cationically polymerizable resin, the photoinitiator system comprising:
  (i) an iodonium salt;
  (ii) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof;
  (iii) a first anthracene and a second anthracene both having the following structure:

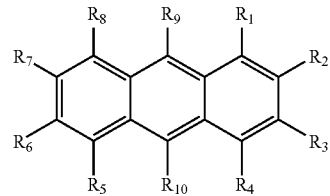

wherein for said first anthracene each of $R_1$ to $R_{10}$ is independently selected from H, alkyl, phenyl or alkoxy groups, provided that at least one of $R_1$ to $R_{10}$ is alkoxy, and
wherein for said second anthracene each of $R_1$ to $R_{10}$ is independently selected from H, alkyl, phenyl or alkoxy groups.

35. The photopolymerizable composition according to claim 34, wherein the cationically polymerizable resin is selected from the group consisting of epoxy, oxetane, vinyl ether and spiro-orthocarbonate resins, and combinations thereof.

36. The photopolymerizable composition according to claim 35, wherein the cationically polymerizable resin comprises an epoxy resin.

37. The photopolymerizable composition according to claim 36, wherein the cationically polymerizable resin comprises a silicon-containing epoxy resin.

38. The photopolymerizable composition according to claim 35, wherein the cationically polymerizable resin comprises a blend of a silicon-containing epoxy resin and an epoxy resin that does not contain silicon.

39. The photopolymerizable composition according to claim 34, wherein the iodonium salt is selected from the group consisting of diaryliodonium hexafluorophosphate, diaryliodonium hexafluoroantimonate, diaryliodonium tetrakis(pentafluorophenyl)borate, 4-octyloxyphenyl phenyliodonium hexafluoroantimonate, 4-(2-hydroxytetradecyloxyphenyl) phenyliodonium hexafluoroantimonate, 4-(1-methylethyl)phenyl 4-methylphenyliodonium tetrakis (pentafluorophenyl)borate, and combinations thereof.

40. The photopolymerizable composition according to claim 34, wherein the visible light sensitizer is an alpha-diketone.

41. The photopolymerizable composition according to claim 40, wherein said alpha-diketone is camphorquinone.

42. The photopolymerizable composition according to claim 34, wherein first anthracene is selected from 2-ethyl-9,10-dimethoxyanthracene, 9,10-diethoxyanthracene, and 1,4-dimethoxyanthracene.

43. A photopolymerizable composition according to claim 34, wherein second anthracene is selected from 2-ethyl-9,10-dimethoxyanthracene, 9,10-dimethylanthracene, 9,10-diethoxyanthracene, 1,4-dimethoxyanthracene, 9-methylanthracene, 2-ethylanthracene, 1,4-dimethoxyanthracene, 2-tert-butylanthracene, 2,6-di-tert-butylanthracene, and 9,10-diphenyl-2,6-di-tert-butylanthracene.

44. A photopolymerizable dental material comprising the photopolymerizable composition of claim 2, 24 or 34.

45. The photopolymerizable dental material of claim 44 further comprising at least one filler.

46. The photopolymerizable dental material of claim 45, wherein said filler is selected from quartz, submicron silica, and non-vitreous microparticles.

47. The photopolymerizable dental material of claim 44, further comprising at least one adjuvant.

48. The photopolymerization dental material of claim 47, wherein said adjuvant is selected from accelerators, inhibitors, absorbers, stabilizers, pigments, dyes, viscosity modifiers, surface tension depressants and wetting aids, antioxidants.

49. A method for preparing a dental restorative or prosthesis, said method comprising:
(a) providing the photopolymerizable dental material of claim 44; and
(b) polymerizing the dental material by exposing it to light of an appropriate wavelength to provide said dental restorative or prosthesis.

50. The method of claim 49, further comprising the step of disposing said material into the mouth of a patient before or after step (b).

51. The method of claim 49, wherein said dental material is irradiated with light for a period of time less than 120 seconds.

52. A photoinitiator system comprising:
(a) an iodonium salt;
(b) a visible light sensitizer selected from the group consisting of ketones, coumarin dyes, xanthene dyes, fluorone dyes, fluorescein dyes, aminoketone dyes, p-substituted aminostyryl ketone compounds, and combinations thereof; and
(c) an electron donor selected from the group consisting of (i) the combination of a first anthracene that has a light absorption maximum less than about 400 nanometers and a second anthracene having the following structure

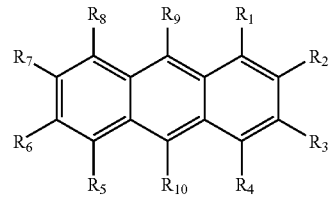

wherein each of $R_1$ to $R_{10}$ is independently selected from H, or alkyl, phenyl or alkoxy groups, provided that at least one of $R_1$ to $R_{10}$ is not H; and (ii) the combination of a first anthracene and a second anthracene both having the following structure:

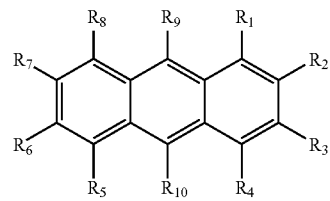

wherein for said first anthracene each of $R_1$ to $R_{10}$ is independently selected from H, alkyl, phenyl, or alkoxy groups, provided that at least one of $R_1$ to $R_{10}$ is alkoxy, and wherein for said second anthracene each of $R_1$ to $R_{10}$ is independently selected from H, alkyl, phenyl or alkoxy groups.

53. The photoinitiator system of claim 52, further comprising:
a cationically polymerizable resin so as to form a photopolymerizable composition.

54. The photopolymerizable composition of claim 53, further comprising:
a filler.

* * * * *

UNITED STATES PATENT AND TRADEMARK OFFICE
CERTIFICATE OF CORRECTION

PATENT NO. : 7,537,452 B2
APPLICATION NO. : 11/893457
DATED : May 26, 2009
INVENTOR(S) : Joel David Oxman It is certified that error appears in the above-identified patent and that said Letters Patent is hereby corrected as shown below:

Column 1
Line 11            Delete "7,626,228," and insert -- 7,262,228, --, therefor.

Column 2
Line 42 (Approx.)  Delete "photoinitator" and insert -- photoinitiator --, therefor.
Line 66 (Approx.)  Delete "photoiniator" and insert -- photoinitiator --, therefor.

Column 3
Line 55            Delete "claims" and insert -- claims. --, therefor.

Column 6
Line 32            Delete "heptan," and insert -- heptane, --, therefor.
Lines 42-43        Delete "tetramethyidisiloxane;" and insert -- tetramethyldisiloxane; --, therefor.

Column 7
Line 28            Delete "Morflex" and insert -- Morflex) --, therefor.

Column 9
Line 56            Delete "hexacrylate," and insert -- hexaacrylate, --, therefor.

Column 12
Line 37            Delete "acenaphthaquinone," and insert -- acenaphthoquinonc, --, therefor.

Column 13
Line 18 (Approx.)  Delete "ethoxy" and insert -- ethoxy. --, therefor.
Line 34            Delete "structure 1," and insert -- structure I, --, therefor.

Signed and Sealed this
Seventeenth Day of January, 2012

David J. Kappos
*Director of the United States Patent and Trademark Office*

CERTIFICATE OF CORRECTION (continued)
U.S. Pat. No. 7,537,452 B2

<u>Column 21-22</u>
Line 6 (Table 1A)   Delete "236.[2" and insert -- 236.2 --, therefor.